(12) United States Patent
Gleser et al.

(10) Patent No.: US 11,672,289 B2
(45) Date of Patent: Jun. 13, 2023

(54) GLOVE

(71) Applicant: YTY INDUSTRY SDN. BHD., Kuala Lumpur (MY)

(72) Inventors: Maxim Gleser, Hannover (DE); Paul Diers, Aachen (DE)

(73) Assignee: YTY INDUSTRY SDN. BHD., Wilayah Persekutuan (MY)

( * ) Notice: Subject to any disclaimer, the term of this patent is extended or adjusted under 35 U.S.C. 154(b) by 0 days.

(21) Appl. No.: 16/400,630

(22) Filed: May 1, 2019

(65) Prior Publication Data

US 2019/0254368 A1 Aug. 22, 2019

Related U.S. Application Data

(63) Continuation of application No. 15/524,325, filed as application No. PCT/DE2015/100458 on Nov. 1, 2015, now abandoned.

(30) Foreign Application Priority Data

Nov. 7, 2014 (DE) .......................... 102014016525.6
Aug. 20, 2015 (DE) .......................... 102015113861.1

(51) Int. Cl.
*A41D 19/015* (2006.01)
*A41D 19/00* (2006.01)
(Continued)

(52) U.S. Cl.
CPC ... *A41D 19/0093* (2013.01); *A41D 19/01547* (2013.01); *A61B 42/00* (2016.02); *A61B 42/50* (2016.02); *A41D 19/0062* (2013.01)

(58) Field of Classification Search
CPC .......... A41D 19/01547; A41D 19/0093; A41D 19/0062; A61B 42/00; A61B 42/50
See application file for complete search history.

(56) References Cited

U.S. PATENT DOCUMENTS 2,075,550 A 3/1937 Smith
2,325,482 A * 7/1943 Curran ............... A41D 19/0034
2/159

(Continued)

FOREIGN PATENT DOCUMENTS

DE 29919345 10/2000
EP 2387896 11/2011
(Continued)

OTHER PUBLICATIONS

International Search Report dated Jan. 25, 2016 in PCT/DE2015/100458.
(Continued)

*Primary Examiner* — Robert H Muromoto, Jr.
(74) *Attorney, Agent, or Firm* — Fox Rothschild LLP

(57) ABSTRACT

The invention relates to a glove having at least one gripping aid arranged at the periphery of the cuff, the surface of which gripping aid at least partially has patterning, especially knobs and/or grooves, wherein the glove at least two of the total five finger spaces which are adapted to the fingers of a hand also has a structured surface or patterning, respectively, especially knobs and/or grooves, essentially at the ends of each finger space opposite the cuff which are provided for intake of the fingertips.

7 Claims, 6 Drawing Sheets

Figure 1:
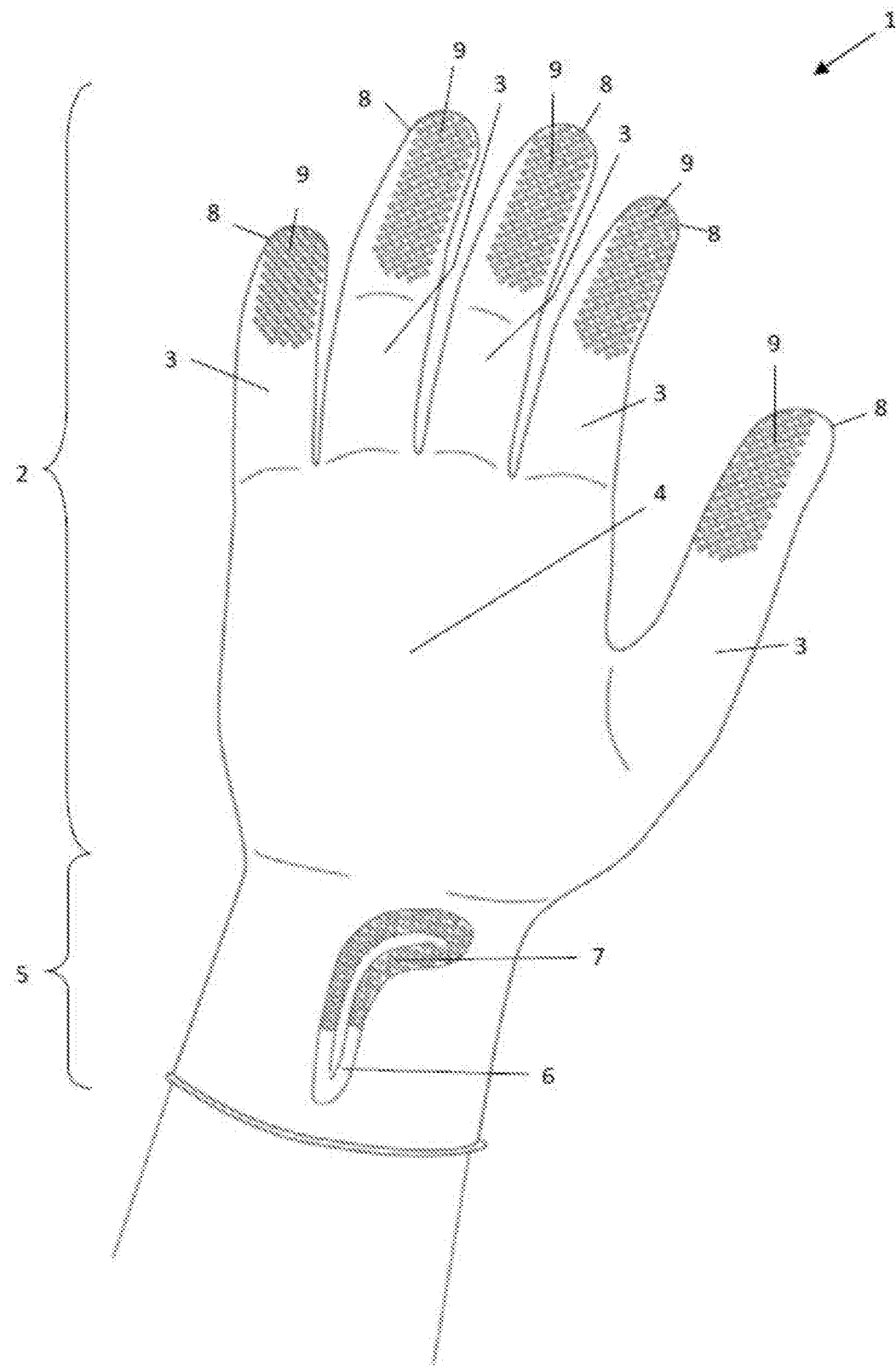

(51) Int. Cl.
*A61B 42/50* (2016.01)
*A61B 42/00* (2016.01)
*A41D 13/08* (2006.01)

(56) References Cited

U.S. PATENT DOCUMENTS

| | | | |
|---|---|---|---|
| 3,341,861 A | 9/1967 | Robbins | |
| 4,399,567 A * | 8/1983 | Weon Joong | A41D 19/0082 2/16 |
| 4,464,796 A * | 8/1984 | Heissenberger | A41D 19/0062 2/162 |
| 4,876,747 A * | 10/1989 | Coffey | A41D 19/0093 2/168 |
| 5,020,160 A * | 6/1991 | Cano | A41D 19/0093 2/158 |
| 5,365,608 A * | 11/1994 | Flick | A41D 19/0003 2/161.7 |
| 5,566,394 A | 10/1996 | Flick | |
| 5,579,539 A * | 12/1996 | Flick | A41D 19/0003 2/161.7 |
| D605,377 S | 12/2009 | House | |
| 7,624,455 B1 * | 12/2009 | Bhalla | A41D 19/0055 2/160 |
| D707,895 S | 6/2014 | Moreland et al. | |
| 9,079,050 B2 * | 7/2015 | Bedetti | A62B 17/003 |
| D745,999 S | 12/2015 | Sood | |
| D765,317 S | 8/2016 | Megat Abdul Aziz et al. | |
| D780,379 S | 2/2017 | Schroedl | |
| 9,622,523 B2 | 4/2017 | Champagne et al. | |
| D827,245 S | 9/2018 | Johnson | |
| 10,470,832 B1 * | 11/2019 | Jones | A41D 19/0082 |
| D919,929 S | 5/2021 | Jones | |
| 2007/0061942 A1 | 3/2007 | Schroedl | |
| 2011/0030121 A1 | 2/2011 | Smalls | |
| 2013/0067638 A1 * | 3/2013 | Patkov | A41D 19/01505 2/168 |
| 2015/0143607 A1 | 5/2015 | Ramirez | |
| 2015/0143610 A1 * | 5/2015 | Pimentel de Oliveira | A41D 19/01547 2/167 |
| 2015/0257835 A1 * | 9/2015 | Le Blanc | A61B 42/50 2/161.7 |
| 2015/0320127 A1 | 11/2015 | Wegner et al. | |
| 2016/0100638 A1 | 4/2016 | Megat Abdul Aziz et al. | |
| 2017/0099892 A1 | 4/2017 | Palese | |

FOREIGN PATENT DOCUMENTS

| | | | |
|---|---|---|---|
| WO | WO9525428 | * | 9/1995 |
| WO | 2000019847 | | 4/2000 |
| WO | 2005036997 | | 4/2005 |

OTHER PUBLICATIONS

Shenning Medical Blend nitrile gloves, posted at medicalexpo.com, posting date not given, [online], [site visited Mar. 24, 2022]. Available from Internet, URL: https://www.medicalexpo.com/prod/shenning-medical/product-129020-1022969.html (Year: 2022).

Freedom IV Exam Glove, posted at ytygroup.com.my, posting date not given, [online], VHJFG6.

Kimberly-Clark Purple Nitrile Exam Disposable Glove, posted at hansler.com, posting date not given, [online], [site visited Mar. 24, 2022], Available from Internet, URL: https://www.hansler.com/collections/gloves/products/kimberly-clark-purple-nitrile-exam-gloves (Year: 2022).

Nitrile Examination Gloves, posted at fishersci.com, posting date not given, [online], [site visited Mar. 24, 2022]. Available from Internet, URL: https://www.fishersci.com/shop/products/nitrile-examination-gloves-19/12888550B (Year: 2022).

* cited by examiner

GLOVE

CROSS-REFERENCE TO RELATED APPLICATIONS

This application is a continuation of U.S. application Ser. No. 15/524,325, filed May 4, 2017, which is a § 371 national stage entry of International Application No. PCT/DE2015/100458, filed Nov. 1, 2015, which claims priority to and the benefit of German Application No. 10 2015 113 861.1 filed Aug. 20, 2015, and German Application No. 10 2014 016 525.6 filed Nov. 7, 2014 all of which are hereby incorporated herein by reference in their entireties.

The invention relates to a glove, especially to an examination glove or to a surgical glove or to a work glove, preferably made of a liquid-impermeable elastic material, which glove in addition to a glove body having five finger spaces and a palm space also comprises a cuff at the surface of which at least one gripping aid is arranged. Furthermore, the invention also relates to a process for production and to the use of the glove as well as to a process for production of formers which are suitable for the production of gloves according to the invention.

STATE OF THE ART

WO 2005/036997 A1 describes a glove having a gripping aid arranged at the cuff, wherein the gripping aid is arranged in the region covering the outer wrist knuckle region of the wrist and/or wherein the gripping aid extends over at least 180° of the periphery of the cuff. Furthermore, there is also described a pair of gloves in which each glove has at least one gripping aid and on both gloves the gripping aids are provided on adjacent peripheral sections of the cuff having an angular distance of at least 30°.

AT 505 712 A1 describes three differing embodiments of gloves. The first embodiment relates to gloves having a gripping aid arranged at the cuff, wherein the tensile modulus of the material of the gripping aid is above 10 MPa (preferably above 100 MPa), or twice as high (preferably ten times as high) as that of the material of the cuff. Accordingly, the material of the gripping aid is different to the material of the cuff.

The second embodiment relates to gloves having at least one gripping aid in the cuff region, wherein the gripping aid is made of the same material as the glove body and connected thereto by a force-fitting connection either directly in the region of the edge of the cuff or on the inside of the glove. A further force-fitting connection is located on the outside of the glove within or above the wrist region.

The third embodiment relates to gloves having a gripping aid which is arranged at an angle of 30° to 150° to the end of the cuff and fastened to the glove by means of at least one and preferably two force-fitting fixation points. As in the first embodiment, the tensile modulus of the material of the gripping aid is above 10 MPa (preferably above 100 MPa) or twice as high (preferably ten times as high) as that of the material of the cuff.

AT 413 190 B describes a glove having a gripping aid arranged at the cuff. Therein, the gripping aid is provided spaced from the rear edge of the cuff on a peripheral section of the cuff adjoining the portion of the back of the hand on the outer side of the hand.

U.S. Pat. No. 5,579,539 describes gloves having a gripping aid protruding in the cuff region, which gripping aid according to a preferred embodiment is arranged laterally below the thumb in the region of the musculus abductor pollicis longus.

EP 1 675 486 B1 protects a pair of gloves as well as a method for removing a pair of gloves in which each glove has at least one gripping aid, wherein the gripping aids on both gloves are arranged on adjoining peripheral sections of the cuff, having an angular distance of at least 135°. Therein, one gripping aid of one glove is arranged on the outside of the cuff covering the outer wrist knuckle region of the wrist, the other gripping aid is arranged at a different position due to the aforementioned angular distance.

DE 299 19 345 U1 describes protection gloves having a partial plastic coating which comprises knobs for enhancement of the abrasion strength and of the grip. Preferably, the gloves are made of woven or knitted material and have no gripping aid.

OBJECT OF THE INVENTION

In view of the known state of the art it is the object of the present invention to provide an alternative glove and a process for its production, which glove is easy to remove after wearing without the wearer coming into contact with soiling or contaminations on the outside of the glove during the removal process.

GENERAL DESCRIPTION OF THE INVENTION

The invention achieves the object by the features of the claims and especially by a glove having at least one gripping aid arranged at the periphery of the cuff, the surface of which gripping aid at least partially having patterning, especially knobs and/or grooves, wherein the glove at least two of the five finger spaces which are adapted to the fingers of a hand also has a structured surface or patterning, respectively, especially knobs and/or grooves, essentially at their ends opposite the cuff which are provided for intake of the fingertips. For the purposes of the invention, an irregular arrangement of elevations or indentations at the respective location of the glove surface, respectively, is also understood as a structured surface.

Therefore, gloves according to the invention especially differ from gloves known from the state of the art by having a gripping aid having an at least partially structured surface in the cuff region and in addition by having at least partially structured surfaces at the ends of at least two finger spaces, respectively, which are adapted for intake of the fingertips. Due to this design, gloves according to the invention may be removed from the hand of a wearer particularly well and safe, as in the removal process the gripping aid having its at least partially structured surface is gripped by fingertips which also have a structured surface. Thus, an interaction occurs between the structured surfaces in the region of the fingertips and the structured surface arranged on the surface of the gripping aid, e.g. an "interlocking" of two burled surfaces, whereby the grip is increased significantly and the risk of slipping from the gripping aid during the removal of the glove is reduced significantly.

According to one embodiment, a glove according to the invention may have structured surfaces only at the gripping aid and at two to five finger spaces or according to an alternative embodiment, the glove according to the invention may have a structured surface on its entire surface (whereby for the purposes of the invention the outside of the glove is meant which does not have contact with the skin of the wearer when the glove is worn).

Optionally, the material of the glove is thicker in the region of the structured surfaces than in adjoining regions without structured surfaces having the same distance to the rolled edge. The advantage of an enhanced material thickness in the region of the structured surfaces lies in the enhanced tear strength.

In detail, a glove according to the invention has a glove body and a cuff attached thereto and connected thereto, respectively, wherein the glove body comprises five finger spaces for intake of the fingers of a hand as well as a palm space for intake of a palm. It differs from known gloves especially in that on the periphery of the cuff at least one gripping aid is arranged which at its surface or at a portion of its surface has patterning, and furthermore in that the glove at the ends of at least two of the finger spaces opposing the palm space and the cuff, respectively, has patterning, too, which preferably is identical to the patterning on the surface of the gripping aid. According to the invention, the glove is made in one piece, accordingly the gripping aid in particular is an integral component of the glove.

In a preferred embodiment, the glove according to the invention consists of the glove body comprising the palm space and the five finger spaces, at least two of which have structured surfaces, the cuff which is attached to the palm space and the at least one gripping aid having an at least partially structured surface arranged on its periphery.

The material from which the glove is produced may be selected depending on the intended application, i.e. depending on the function to be achieved by the glove and may in particular be acrylonitrile, nitrile, nitrile rubber, polyethylene, polyvinyl chloride, vinyl, polyvinyl alcohol, polyurethane, rubber, caoutchouc, natural rubber, latex, natural latex, neoprene, chloroprene, chloroprene rubber, chloroprene latex, butyl rubber, fluororubber and combinations thereof.

Preferably, at its end opposite the glove body, the cuff of the glove according to the invention has a rolled edge as a border. The rolled edge may have an arbitrary thickness and usually consists of 5 to 6 layers of the rolled-up glove material.

Between the rolled edge and the end of the cuff attached to the glove body the at least one gripping aid is arranged at an arbitrary position on the periphery of the cuff, wherein it can also be arranged directly at one or both ends of the cuff, i.e. directly at or in immediate proximity to the rolled edge and/or directly at or in immediate proximity to the end attached to the glove body. An arrangement of the at least one gripping aid at or in immediate proximity to the rolled edge is preferred, as with this arrangement the force upon pulling is transmitted onto the rolled edge during the removal process and the gloves therefore have an enhanced tear strength. A further advantage of the arrangement of the gripping aid at or in immediate proximity to the rolled edge lies in that the wearer in the beginning of the removal process, i.e. upon inserting a hand with the fingertips first into the glove, naturally holds the thumb tight to the palm, whereas he laterally moves the thumb next to the palm as soon as the hand is inserted further into the glove. Therefore, with a gripping aid arranged at or in immediate proximity to the rolled edge there exists a reduced risk that the wearer with his thumb gets caught in the cavity formed by the gripping aid and the glove is damaged by that.

Optionally, the gripping aid of the glove has smaller dimensions than the finger space which is adapted to a thumb, especially having a (for example by 10-30%) smaller perimeter and/or a smaller diameter, for example a diameter which is smaller by at least 20%. Further optionally, the length of the gripping aid perpendicular to its perimeter is smaller than the average distance between a tip of a thumb and the first thumb joint of an adult. The length of the gripping aid (measured from its attachment at the cuff to its opposing end) therefore amounts to preferably less than 3 cm, especially less than 2.5-2.7 cm. By the aforementioned preferred dimensions of the gripping aid it shall be ensured that the thumb of the wearer does not get into the gripping aid when putting on the glove, whereby the glove could be damaged.

According to a particularly preferred embodiment, a glove according to the invention has exactly one gripping aid having an at least partially structured surface. When the glove is put on, this gripping aid is arranged in the cuff region laterally of the wrist. Therefore, in a vertical arrangement of the glove with the finger spaces pointing upwards, a possible arrangement of the gripping aid is below the finger space which is adapted for intake of a thumb. A less preferred alternative arrangement of the gripping aid in a vertical arrangement of the glove with the finger spaces pointing upwards is below the finger space which is adapted for intake of a little finger. In this preferred embodiment having a gripping aid arranged laterally of the wrist, a glove according to the invention is particularly suitable for an ambilateral wearability, i.e. the glove may be worn on a left hand as well as on a right hand, wherein the position of the gripping aid on each hand is identical, respectively, namely either laterally of the wrist below the thumb or laterally of the wrist below the little finger.

Therein, for the purposes of the invention, the expression "laterally of the wrist" means a position at one of the both narrow sides of the wrist when the gloves are put on, wherein it is assumed that each wrist has two longitudinal sides and two narrow sides, wherein, when the hand is arranged vertically with the fingertips pointing upwards, one longitudinal side is arranged below the back of the hand and the other one is arranged below the palm and the narrow sides are arranged opposite to one another between the two longitudinal sides.

Furthermore, in addition to the ambilateral wearability of the gloves according to the invention having a gripping aid arranged laterally of the wrist, this arrangement also has the advantage that the gloves may be packed into cartons in larger quantities in a better way, e.g. every 100 pieces. This is because on the one hand gloves having the gripping aid arranged accordingly may be packed in a space-saving way, as no additional layer of glove material results from the gripping aid. On the other hand, with gloves having a gripping aid arranged laterally of the wrist when the glove is worn, the gripping aid is not flattened during stacking in a carton.

As a further advantage of a gripping aid which is arranged in the cuff region laterally of the wrist when the glove is worn, measurements using a dynamometer have revealed that with the aforementioned arrangement of the gripping aid an effort of the wearer of the glove reduced by 4% is required for removing the gloves from the hand by gripping the gripping aid after usage.

In one embodiment, gloves according to the invention have an increased wall thickness at the gripping aid when compared to the rest of the glove, especially at the transitions between the gripping aid and the rest of the glove. This is produced in that upon dipping of the formers into an immersion bath one or more notches are there on the elevation through which the gripping aid is produced. In this at least one notch the liquid from the immersion bath accumulates increasingly such that during the subsequent drying of the gloves regions having an increased wall thickness are generated at the positions of the notches. Due to the increased material thickness at this position the corresponding regions also have a modified look when compared to the rest of the glove, as they are usually darker than the rest of the glove. This provides the additional advantage of a visual signaling effect which is supposed to remind the wearer to seize the gloves only at the gripping aid for removal from the hand.

The shape of the at least one gripping aid is variable, wherein the gripping aid especially may be formed essentially knob-shaped, lobular, band-shaped, tongue-shaped, pyramid-shaped, cone-shaped, truncated cone-shaped or angular. Preferably, the gripping aid is an elevation on the surface of the cuff, which, when the glove is put on, i.e. when the glove is worn on the hand, unlike the rest of the glove does not fit tight to the hand but is projecting from the surface of the glove, especially in the shape of a lobe, wherein a cavity is formed especially between the inner side of the lobe and the hand of the wearer. Apart from the dimensions the aforementioned cavity formed by the gripping aid does not differ significantly from the cavities which are formed by the five finger spaces. Especially, the glove does not have any air bubbles, edges or other irregularities in the region of the gripping aid when it is worn.

In one embodiment the gripping aid is in the shape of a lobe which is arranged angularly on the periphery of the cuff, wherein the angle is for example an acute angle or a right angle and especially an obtuse angle, one leg of which runs about perpendicularly to the rolled edge forming the end of the cuff and especially at a spacing thereto, wherein the other leg, starting from the vertex, runs in the direction of the finger space which is adapted for intake of a thumb or adapted to a thumb, respectively. This angular arrangement of the gripping aid on the periphery of the cuff is particularly ergonomically as for removal, the gripping aid can be gripped particularly well at about the vertex of the gripping aid with the thumb and at least one further finger and can be pulled off the hand of the wearer. A further advantage of a gripping aid as a lobe which is arranged angularly on the periphery of the cuff lies in that during the removal the gripping aid does not stretch and thereby is clearly visible and seizable.

Figure 6:
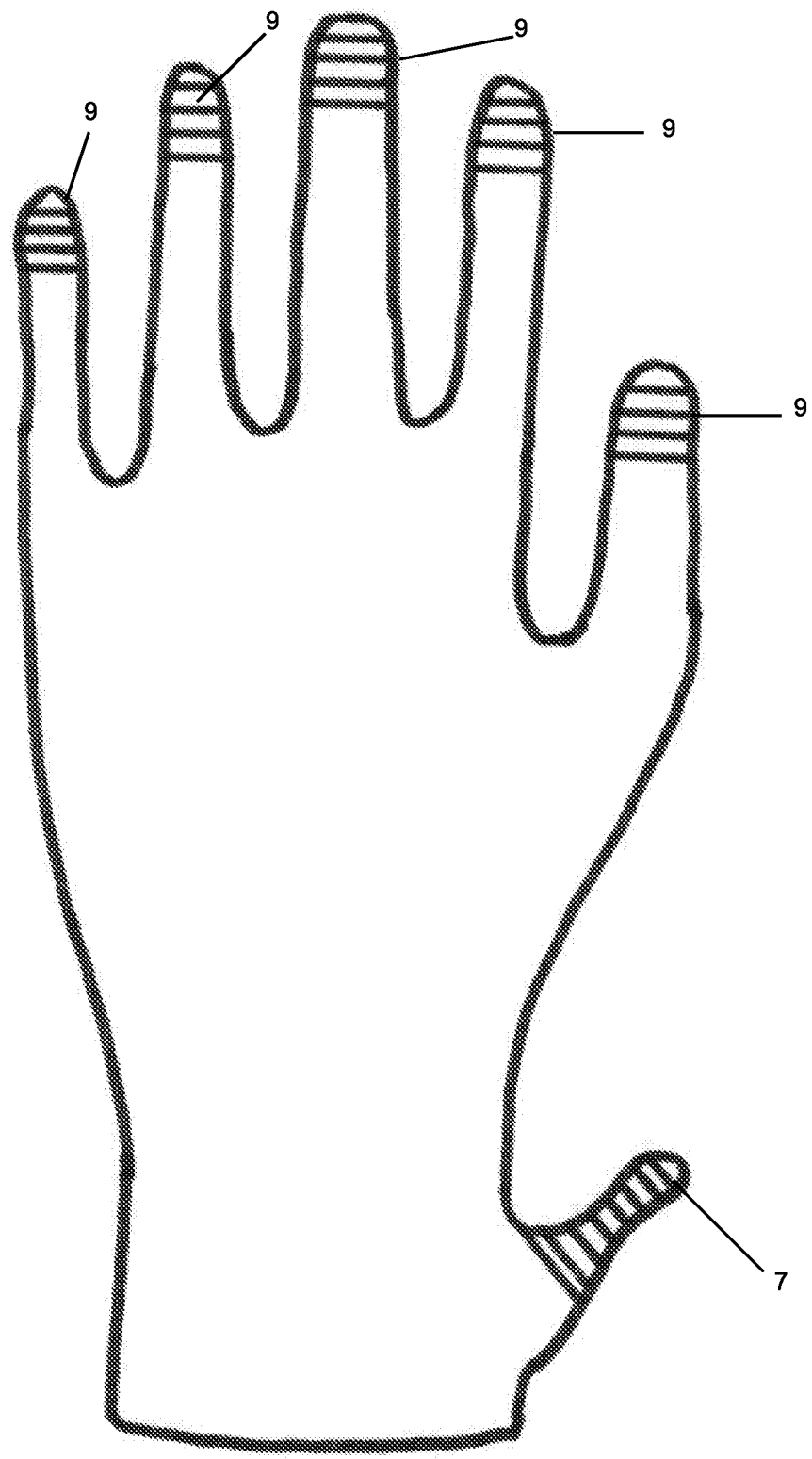

According to a preferred embodiment, the gripping aid has a shape which is similar to a truncated cone and is arranged laterally of the wrist when the glove is worn, preferably below the finger space which is adapted for intake of a thumb. Preferably, the gripping aid has a depression on its side averted from the cuff, e.g. as it is depicted in FIG. 6, in which depression the material thickness preferably is increased.

Furthermore, the invention also relates to a pair of gloves consisting of two gloves according to the invention. These two gloves according to the invention can be identical or can differ from one another.

In order to ensure that the wearer does not slip during the removal of one glove while seizing the glove with the other hand, the surface of the gripping aid of a glove according to the invention is at least partially structured, wherein the glove according to the invention preferably has a structured surface on the entire gripping aid. This structured surface preferably has elevations and indentations which especially are arranged regularly, for example grooves, lamellae, flutings, especially running in parallel, or lozenges, squares or knobs at a regular spacing. In particular, the aforementioned patterning not only gives an increased grip to the gripping aid upon touching, but also an increased stability which facilitates the seizing with the other hand, respectively. Preferably, the area of the structured surface at the gripping aid amounts to at least 0.1 to 0.5 $cm^2$, more preferred to at least 1 $cm^2$ and particularly preferred to at least 2 $cm^2$.

In one embodiment, the gripping aid has two or more regions of structured surfaces, which are separated from one another by regions having non-structured surfaces. This involves the advantage of an increased tear strength, as especially with gloves in which the gripping aid is arranged directly at or in the proximity to the rolled edge forming the end of the cuff, a superior transmission of power onto the rolled edge occurs by the non-structured regions. An increased tear strength in comparison to conventional gloves having a gripping aid or without gripping aid allows a more frequent reuse with gloves that are certified therefor.

In addition to the structured surface at the gripping aid, gloves according to the invention also have at least one structured surface at least two finger spaces, respectively, especially at the finger space which is adapted for intake of a thumb as well as at least one further finger space. Therein, the structured surface at each of these finger spaces is especially arranged at the respective ends of the finger spaces opposite the palm space, which finger spaces are adapted for intake of the respective outer finger phalanges. At the same time, the patterning at the finger spaces are arranged either fully circumferential or only partially circumferential at the respective ends of the finger spaces. In the case of a structured surface which is arranged only partially circumferential at the ends of the finger spaces, the structured surface can form one or more areas having a structured surface, wherein more structured surfaces are connected to one another through surfaces without patterning. It is preferred that the area of each structured surface on a finger space has a size of at least 0.1 to 0.5 $cm^2$, more preferred of at least 1 $cm^2$ and particularly preferred of at least 2 $cm^2$.

Like the structured surface of the gripping aid, the structured surface at the finger spaces preferably has elevations and indentations, too, which in particular are arranged regularly, for example grooves, flutings, lamellae, especially running in parallel, or lozenges, squares or knobs at a regular spacing.

The structured surface of the gripping aid has patterning that is identical to or differing from that of the structured surface at the at least two finger spaces.

With identical patterning, e.g. knobs, at the gripping aid and at the finger spaces, respectively, a glove wearer seizes the nubby surface of the gripping aid at one glove with the also nubby surfaces at least two finger spaces of the other glove when removing the gloves. Therefore, the patterning interlock and therein allow a particularly stable grip during the removal. However, differing patterning at the gripping aid and at the finger spaces also allow a stable grip and therein a safe removal of the gloves when having a respective coordination of the patterning to one another. For example, with differing patterning the structured surface at the finger spaces could have knobs which interlock with a latticed patterning at the structured surface of the gripping aid.

In one embodiment, the structured surface at the finger spaces and/or the structured surface at the gripping aid has a color which differs from the rest of the glove, especially a signal color, e.g. red. Thus, during removal, the wearer is reminded by the visual peculiarity to seize the structured surface of the gripping aid with the structured surfaces of the finger spaces and to avoid slipping and therein the risk of contaminations, especially of the forearm or of the wrist, through the optimal hold of the glove between both structured surfaces.

Preferably, for an ambilateral wearability gloves according to the invention have a fully circumferential structured surface at the ends of at least two finger spaces, especially at the finger space adapted to a thumb as well as at least one further finger space. Especially, gloves according to the invention have fully circumferential structured surfaces at the finger space which is adapted to a thumb or at its end, respectively, as well as at the two finger spaces adjacent thereto (for intake of index finger and middle finger). Particularly preferred, identically structured surfaces are arranged fully circumferentially at the ends of each of the five finger spaces.

For the purposes of the invention, the arrangement of two structured surfaces at the ends of the finger spaces, which surfaces are spaced by about 180° on the periphery of the finger spaces and are connected to one another through a non-structured surface, is also understood as a fully circumferential arrangement of the structured surfaces at the ends of the finger spaces.

With gloves according to the invention that can be worn ambilaterally, it is a fact that according to one embodiment two gripping aids having an at least partially structured surface are arranged on the periphery of the cuff, the gripping aids being spaced to one another on the periphery of the cuff by essentially 180°. Thus, it holds true that when the glove is worn it has a gripping aid at the inner side of the wrist and at the outer side of the wrist on each hand, respectively.

Therefore, according to this embodiment a glove according to the invention which can be worn ambilaterally preferably consists of the glove body having the palm space and five finger spaces having fully circumferential structured surfaces at their ends opposite the cuff, as well as the cuff attached to the palm space, on the periphery of which cuff two gripping aids having a structured surface are arranged at a distance of essentially 180°.

In less preferred embodiments, alternatively more than two, e.g. three or four or more gripping aids can be arranged on the periphery of the cuff, especially having the aforementioned structured surfaces, respectively.

In general, the gloves according to the invention comply with the standards and requirements which are demanded for gloves in their respective application. For example, medical gloves, e.g. examination gloves or surgical gloves, have an AQL value of max. 2.5 and especially of 1.5 to 2 or below 1.5.

In particular, depending on the intended application, gloves according to the invention can also comprise usage hints and/or identifiers which are arranged at an arbitrary location. For example, usage hints which are supposed to remind the wearer to seize the glove at the gripping aid for removal can be arranged directly on the gripping aid or in the region adjacent thereto.

In the palm region, gloves according to the invention preferably have a wall thickness of about 0.03 to 0.15 mm, whereas their wall thickness in the region of the finger spaces preferably is 0.07 to 0.2 mm. Thereby, even ultrathin gloves according to the invention resist a tensile force of more than 6 newtons, especially a tensile force starting at the gripping aid.

Further, the invention also relates to a process for production of gloves having a glove body which comprises five finger spaces and a palm space connected thereto and having a cuff attached to the palm space, at the periphery of which cuff at least one gripping aid is arranged, wherein the glove body, the cuff and the at least one gripping aid are made in one piece, the gripping aid has an at least partially structured surface and the glove body has a structured surface at least two of the finger spaces at their respective ends opposite the palm space.

Like conventional gloves, the gloves in the process according to the invention are produced by means of formers which are dipped into an immersion bath, e.g. comprising or consisting of acrylonitrile, and subsequently are dried, vulcanized and removed from the formers, e.g. using compressed air.

After the dipping of the formers into the immersion bath, the so-called "dipping", which usually is carried out with the fingertips of the model hand first, the formers are left to dry preferably in the same position, i.e. with the fingertips pointing downwards. Thus, gloves having an increased material thickness in the region of the fingertips are produced. Alternatively, the formers may also be rotated by 90-180° after dipping into the immersion bath, such that the liquid used in the immersion bath does not accumulate at the fingertips of the model hand, but at least partially runs in the opposite direction, i.e. in the direction of the cuff, therein being distributed in a superior way. In this way, gloves having a more regular material thickness are produced.

A rotation of the formers after the dipping into the immersion bath, especially by 90°, makes sense also in view of the reason that after drying the gloves can be stripped off the formers in a better way. As such a rotation of the formers after drying may not readily be possible in the same production line in which the formers after the dipping into the immersion bath are left to dry without rotation, according to the invention the formers can be arranged on the production line using a transition piece. Therefore, in this embodiment the process according to the invention comprises a step of arranging the formers onto transition pieces which are attached to the production line, respectively, prior to the dipping of the formers into the immersion bath.

With gloves known from the state of the art having a gripping aid there is often exhibited the problem that these have a wall thickness which is too low in the region between the finger spaces which are adapted to a thumb and to an index finger as well as in the region between the gripping aid and the finger space which is adapted to a thumb (both regions are denoted as "crotch area"), as the liquid which is in the immersion bath, which liquid upon dipping of the formers into the immersion bath adheres to these, is partially intercepted by the gripping aid, such that too little liquid runs into the two aforementioned regions denoted as "crotch area".

In order to avoid this problem with the gloves according to the invention, the formers used in the process according to the invention preferably have a reservoir for liquid from the immersion bath, in which reservoir liquid assembles during the dipping of the formers. After removing the formers from the immersion bath, this liquid runs into the region between the finger spaces which are adapted to a thumb and to an index finger, as well as into the region between the gripping aid and the finger space adapted to a thumb by means of specific rotary and/or tilting movements of the formers.

Alternatively or in addition thereto the formers used in the process according to the invention have regions having a preferred direction of flow in comparison to formers known from the state of the art. These can be e.g. regions having inclinations through which liquid adhering to the formers after their removal from the immersion bath increasingly runs in the direction of the region of both aforementioned "crotch areas".

However, the aforementioned regions having a preferred direction of flow may also be formed by a selective arrangement of the structured surfaces on the gripping aid. After the dipping of the formers into the immersion bath the drying usually occurs in a vertical position with fingertips and finger spaces pointing downwards, respectively. Therefore, because of the gravity liquid adhering to the formers also runs downwards in the direction of the fingertips and finger spaces, respectively. Because of the patterning at the gripping aid, the liquid adheres to these at the gripping aid in a superior way and preferably accumulates in the region of the transition between the patterning and the adjoining non-structured regions in the direction of the rolled edge due to a backlog of liquid flowing downwards. Therefore, it can be achieved by a selective arrangement of knobs or other structured surfaces at the gripping aid that the material from the immersion bath adhering to the formers is redistributed selectively during the step of dripping off and the step of drying, respectively, whereby the material thickness of gloves according to the invention in the region of the "crotch areas" is increased in comparison to gloves having a gripping aid without patterning. The risk of the formation of holes in the region of the "crotch areas" therefore can be minimized by a selective arrangement of structured surfaces on the gripping aid, for example by at least 3% or even by about 3-10%, in comparison to gloves having a non-structured gripping aid, respectively.

In any case, it is necessary for the aforementioned selective arrangement of structured surfaces on the gripping aid that in a vertical position with the fingertips and finger spaces pointing downwards, respectively, the patterning is arranged at least partially above the "crotch area" between the gripping aid and the finger space that is adapted to a thumb, as otherwise the material cannot flow in the direction of the "crotch area" using gravity. For example, the patterning can be arranged essentially parabolic on the gripping aid, wherein in a vertical position of the glove with the fingertips and finger spaces pointing downwards, respectively, the vertex of the parabola is arranged above the "crotch area" between the gripping aid and the finger space which is adapted to a thumb.

Optionally, when dipping into the immersion bath, the formers also have one or more notches on the elevation through which the gripping aid is produced. In this at least one notch the liquid of the immersion bath accumulates increasingly, such that regions having an increased wall thickness are produced at the positions of the notches during the subsequent drying of the gloves. As through the at least one notch enough material from the immersion bath accumulates in the wrist region of the glove during the "dipping", less viscous material, e.g. less viscous latex can be used as liquid for the immersion bath according to an advantageous embodiment. In this embodiment, the subsequent vulcanization can be carried out at lower temperatures than the vulcanization of gloves having a gripping aid with no notches known from the state of the art, for example at by 5-10% lower temperatures. These reduced temperatures cause a saving of costs in the vulcanization step.

In any case, in contrast to conventional production processes for gloves the production process according to the invention is characterized by the provision of formers having the geometry of a hand having an essentially cylindrical section adjoining thereto, on the periphery of which at least one elevation is arranged, wherein at the surface of the elevation patterning is arranged at least partially, especially regularly arranged patterning, and wherein at least two fingers of the model hand at their respective ends opposite the palm patterning is arranged, too. These provided formers, instead of conventional formers having the shape of a hand with a smooth and essentially even surface, are dipped into a bath comprising or consisting of chemical and/or natural ingredients in the usual way, subsequently dried and vulcanized as well as optionally washed and cleaned. Therefore, the process for producing gloves according to the invention is distinguished in that the at least one gripping aid with its at least partially structured surface as well as the structured surfaces at the finger spaces of the glove body are co-produced in the shaping process of the glove.

Optionally, gloves according to the invention are chlorinated during or after the dipping into the immersion bath, whereby the stretch characteristics of the gloves may be varied. For an elongation of 50-100% gloves which are not according to the invention have a stretch modulus of 2.1 MPa (±40%), whereas gloves according to the invention can have a modulus of up to 3.4 MPa (±40%) for a respective elongation.

Further, the process according to the invention comprises a step of separating the gloves from the formers, the so-called "stripping". This step can take place in a completely manual fashion ("manual stripping") or it comprises the stripping of the finished gloves from the formers by means of at least two strippers ("mechanical stripping"). Therein, these strippers, for example brushes or rolls, move on the former from the cuff into the direction of the fingertips of the model hand, wherein the glove is pulled off the former up to the respective height of the strippers. Therein a further advantage of the gripping aid being arranged laterally of the wrist when the glove is worn becomes apparent: with gloves having only one laterally arranged gripping aid there is no risk of the strippers getting caught at the gripping aid, whereby the glove could be damaged as it can be the case with two gripping aids which are arranged opposite to one another above and below the wrist.

Preferably, the step of separating the gloves from the formers also comprises blowing the gloves off the formers using compressed air. Therein it is preferred to blow the compressed air onto the cuff and onto the gripping aid by means of two or more conduits, such that the gloves having the gripping aid come off the formers in a superior way.

Optionally, prior to the step of separating the gloves from the formers, the process according to the invention comprises a step which is called "beading". In contrast to conventional processes, in the beading according to the invention the rolled edge is not rolled up using a relatively large brush, but using two smaller brushes having a diameter which for example is smaller by 10-50% than in brushes used in the "beading" in conventional processes. The advantage of two brushes having a smaller diameter lies in that in the region of the gripping aid, the brushes do not come into contact with uncured material, e.g. with uncured nitrile, whereby the glove might tear.

As an alternative to the aforementioned process for production of gloves according to the invention, the former provided in the process having the geometry of a hand and an adjoining cylindrical section instead of the at least one elevation on the periphery of the cylindrical section can also have at least one indentation on its periphery, wherein at the surface of the indentation patterning is arranged at least partially, especially regularly arranged patterning, especially being indentations again, and wherein at least two fingers of the model hand at their ends opposite the palm, respectively, patterning in the shape of indentations is arranged, too. In this way, the gloves can be turned inside out during the removing from the model hand in the production process according to the invention, whereby the gripping aid having its structured surface protrudes from the surface of the glove, for example in the shape of a lobe.

The invention also relates to a process for production of a former for use in a process for producing gloves according to the invention. This method for production of a former preferably has a step of producing a so-called master mould (=mother mould) which has a similar or identical geometry in comparison to a former but is larger than the former in its dimensions by at least 5-10%, preferably by at least 15%. Therein, the patterning on the gripping aid or on the elevation, respectively, and on at least two of the finger spaces preferably is produced in that the master mould is arranged within a protective cover and is surrounded by a protective cover, respectively, the protective cover having recesses in the region of the desired patterning on the gripping aid or on the elevation, respectively, and at the finger spaces. Subsequently, these recesses, i.e. the surfaces of the master mould which are not surrounded by the protective cover, are treated using a sandblast. Therein, the geometry of the generated patterning can be influenced by the particle size of the grains of sand.

As an alternative to a protective cover having recesses on the gripping aid and on the finger spaces, the master mould can also be arranged within a protective cover having one or more recesses only on the gripping aid or only on the finger spaces, respectively. After the treatment of the at least one recess using a sandblast the grains of which having a first geometry, the protective cover is removed from the master mould and a second protective cover is arranged around the master mould, which also has one or more recesses only on the gripping aid or only on the finger spaces, respectively, but which is sealed in places in which the first protective cover had a recess. By a second treatment using a sandblast the grains of which having a second geometry differing from the first geometry, patterning is generated in the region of the at least one recess, the patterning having a different geometry than the patterning generated by the first treatment with the sandblast. Therefore, by this two-step sandblast treatment using two different protective covers in contrast to an only one-step sandblast treatment, different patterning is produced at the gripping aid than at the finger spaces. By analogy, with a two-step sandblast treatment differing patterning at the gripping aid can also be produced in that the recesses in the protective cover surrounding the master mould in the first step are arranged at a different position than the recesses within the protective cover in the second step. Analogously, two or more different patterning can be generated on gripping aids by multi-step treatment using a sandblast.

Preferably, the aforementioned process for production of a former also comprises a step of producing a negative form by means of the master mould into which a liquid or solid composition is given subsequently, for example a ceramic mixture. In an ensuing drying step, preferably including a temperature treatment, the composition within the negative form shrinks by at least 5-10%, wherein after or by the shrinking to the final size, respectively, the former is obtained.

Usually, the formers are stored in receptacles having individual compartments for intake of one former each. Therein, with the preferred arrangement of the gripping aid laterally of the wrist below the thumb the advantage appears that the size of the individual compartments may be kept all the same, whereas e.g. with a gripping aid which is arranged above and/or below the wrist bigger compartments would be required due to the increased space requirement of the respective formers.

Furthermore, the invention also relates to the use of the gloves according to the invention, especially as examination glove, surgical glove or work glove. As the gloves according to the invention are provided particularly for assurance of a working without contaminations, in view of a good hand hygiene it is also intended to use a disinfectant for the hands after removing the gloves. Therefore, the invention also relates to a kit-of-parts comprising a pair of gloves according to the invention as well as a hand sanitiser.

DETAILED DESCRIPTION OF THE INVENTION

Figure 2:
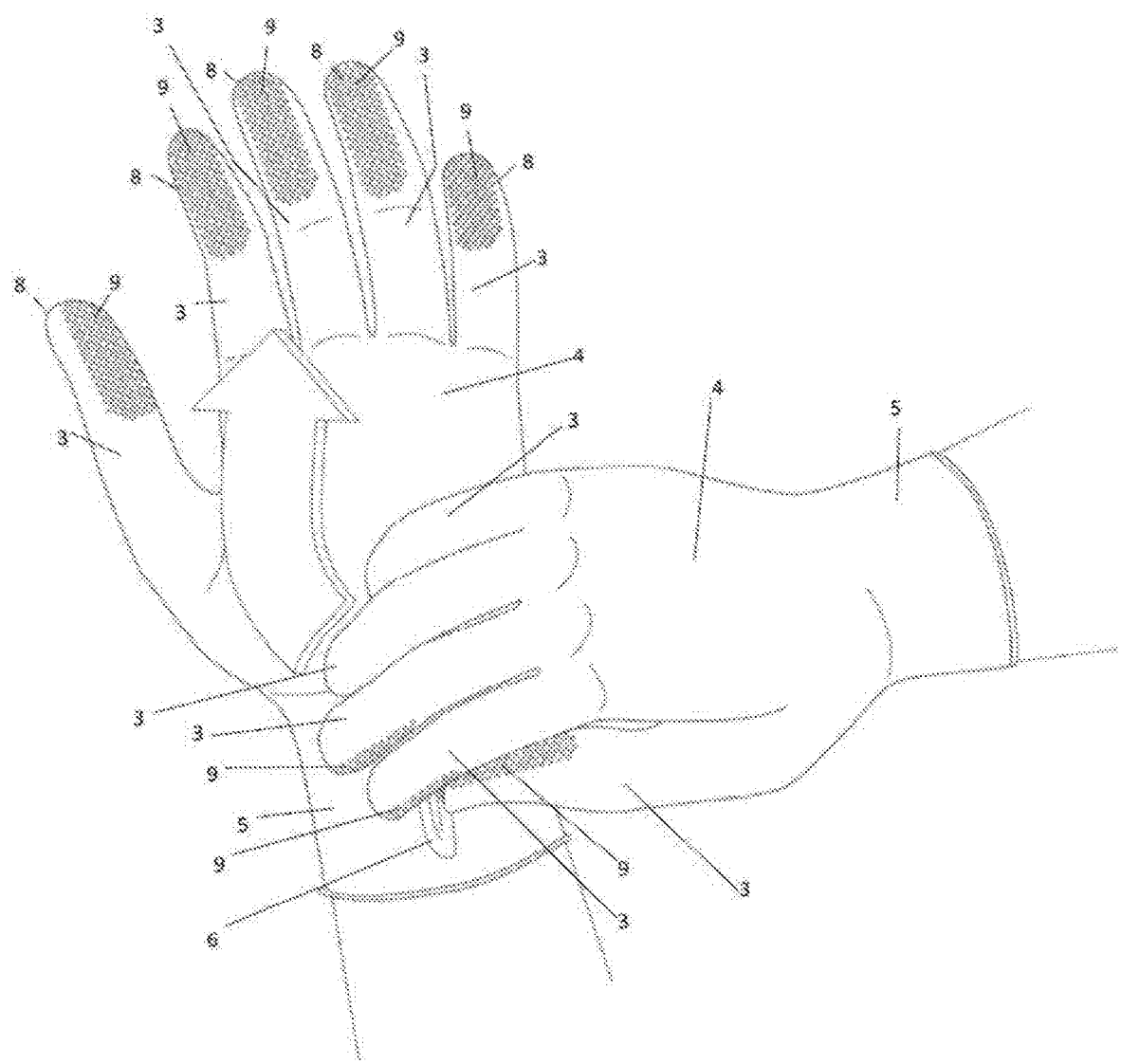
Figure 3:
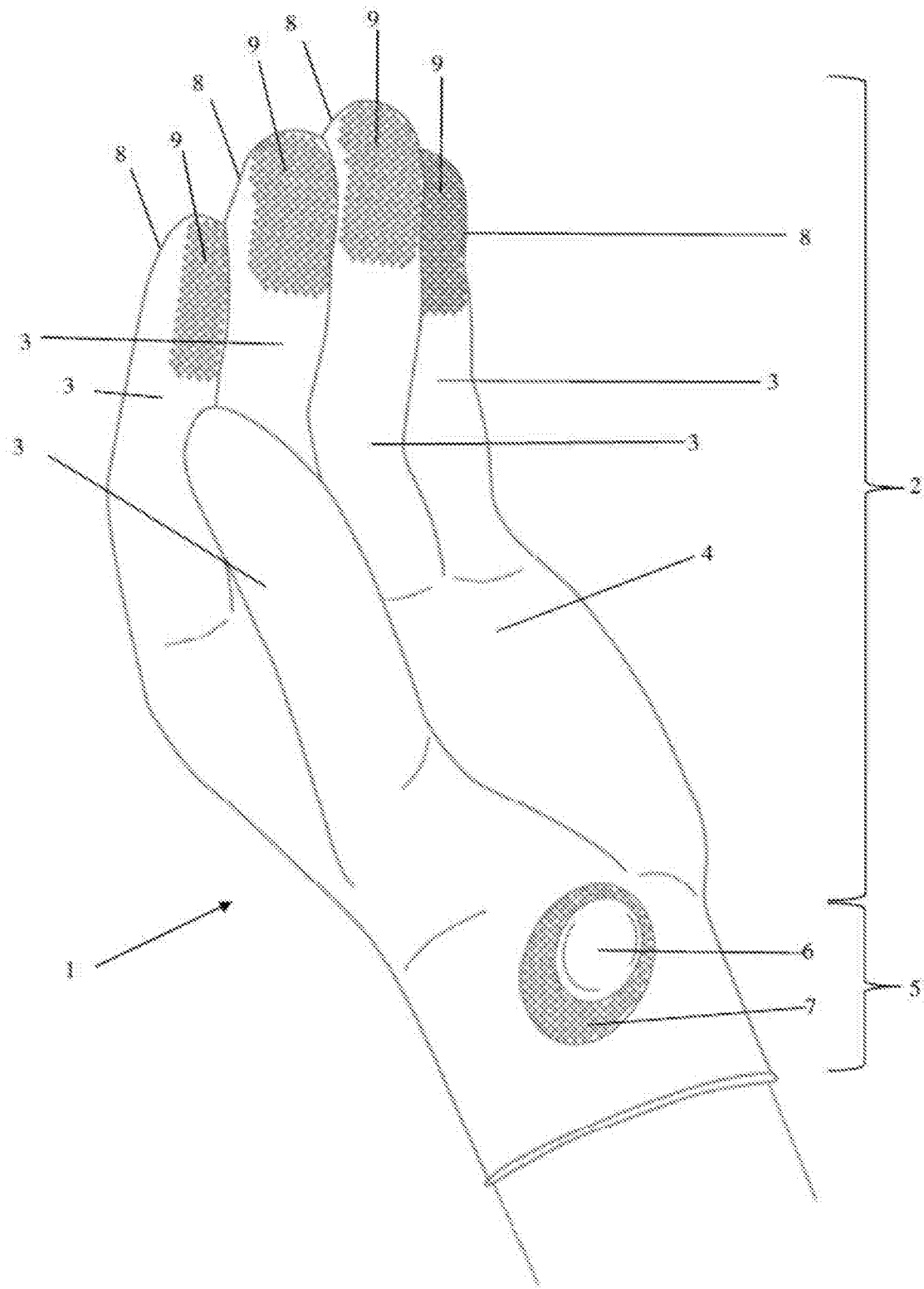
Figure 4:
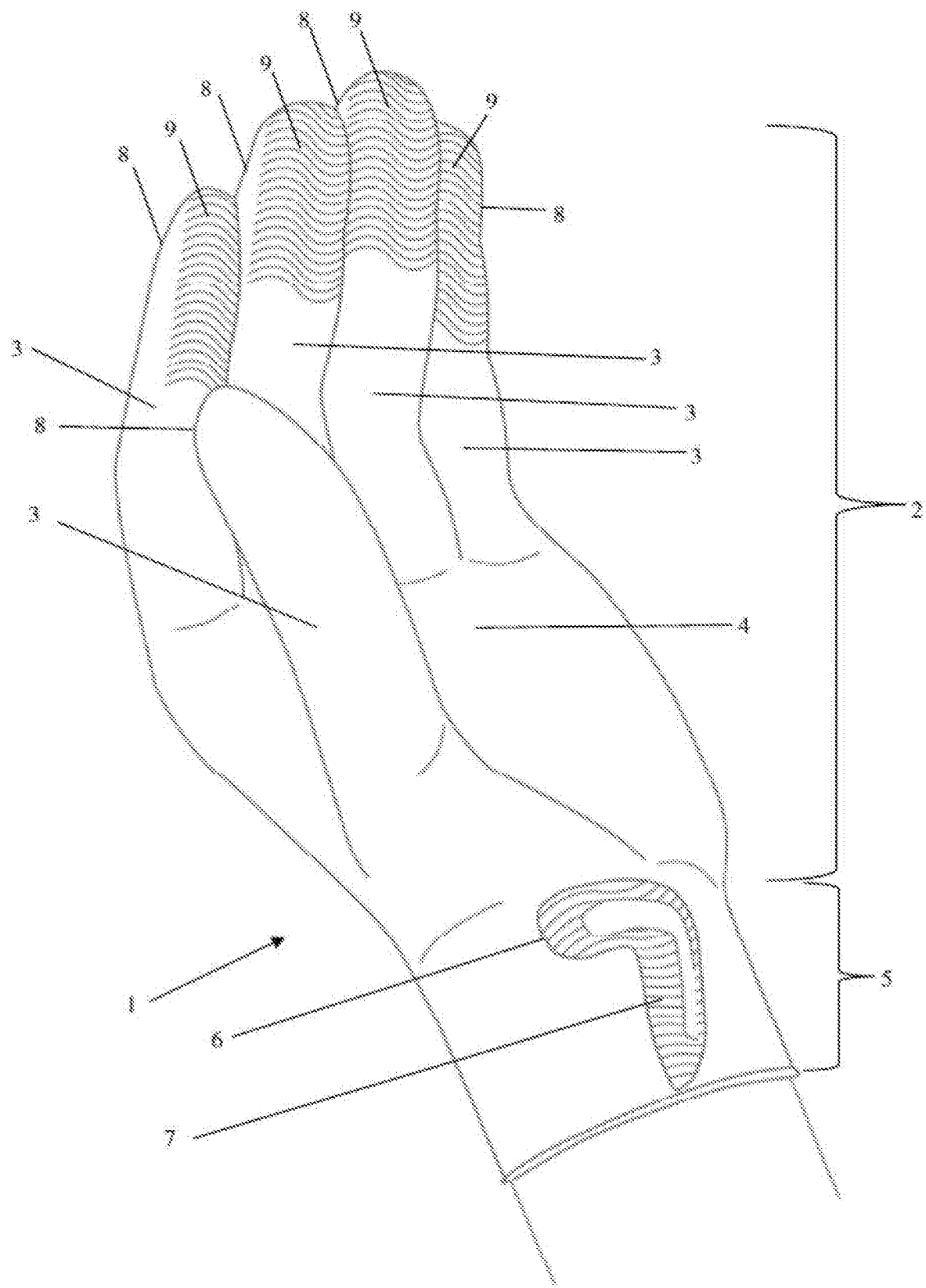
Figure 5:
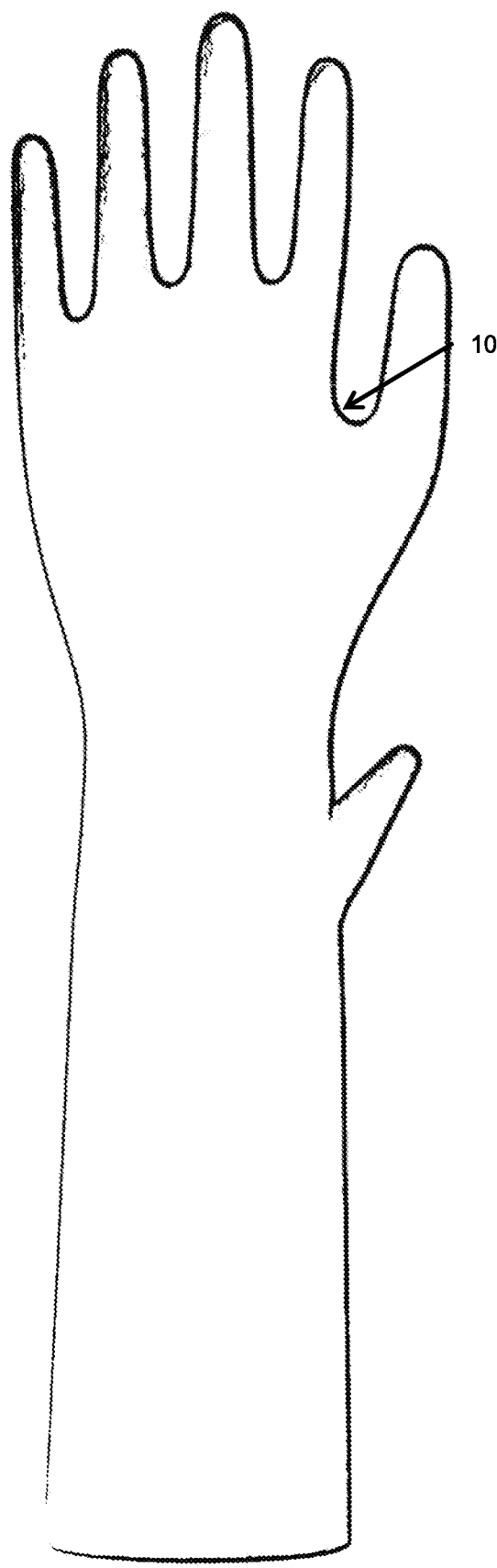

The invention is now described in greater detail by way of examples and with reference to the figures in which FIG. 1 schematically shows a hand wearing a glove according to the invention, FIG. 2 schematically shows the removal process of a glove according to the invention, FIG. 3 schematically shows a hand wearing a further glove according to the invention, FIG. 4 schematically shows a hand wearing a further glove according to the invention, FIG. 5 schematically shows a former applicable in a process according to the invention, and FIG. 6 schematically shows a preferred embodiment of a glove according to the invention.

In the figures, identical reference numerals denote functionally equivalent components.

FIG. 1 shows a glove 1 having a glove body 2 and a cuff 5. The glove body 2 comprises five finger spaces 3 which are connected to the palm space 4 each. At their ends 8 opposite the palm space 4, the finger spaces 3 each have structured surfaces 9. Although generally an arrangement of the structured surfaces 9 on the entire periphery of the finger spaces 3 is preferred at least in the region of their ends 8 opposite the palm space 4, in the depicted embodiment the structured surfaces 9 are arranged only partially circumferential at the ends 8 of the finger spaces 3. The structured surfaces 9 have regularly arranged knobs, respectively, extending from the ends 8 of the finger spaces 3 in the direction of the palm space 4, i.e. when the glove is worn being located at the fingertips of the respective outer phalanges or also of the phalanges adjacent thereto, respectively.

At the cuff 5, an angularly arranged lobular gripping aid 6 having a partially structured surface 7 is arranged. One portion or leg, respectively, of the angular gripping aid 6 is arranged on the periphery of the cuff at a spacing to and essentially in perpendicular to the rolled edge forming the end of the cuff 5, extending over about 50-70% of the length between the rolled edge and the opposite end of the cuff 5 which adjoins to the palm space 4. The second portion or leg, respectively, of the angular gripping aid 6 is arranged at an obtuse angle of about 110° to the first portion or leg, respectively, extending in the direction of the thumb and the finger space 3 which is adapted to a thumb, respectively.

FIG. 2 shows the removal process with the glove 1 according to the invention depicted in FIG. 1. In the depicted embodiment, the gloves for the right and for the left hand are not identical and therefore cannot be worn ambilaterally, as the knobs at the ends 8 of the finger spaces 3 which knobs form the structured surfaces 9 are arranged only at one side of the finger spaces 3, respectively, and therefore extend over only about 20 to 50% of the periphery of the ends of each finger space 3.

In the depicted embodiment, the gripping aid 6 of the left glove is seized at its structured surface 7 by a right hand such that the structured surfaces 9 at the ends 8 of the finger spaces 3 interact with the structured surface 7 of the gripping aid 6, i.e. for an increased grip the knobs of the structured surface 7 and the knobs of the structured surfaces 9 intertwine.

FIG. 3 shows a glove according to the invention having a knob-shaped gripping aid 6 having a structured surface 7 which in the depicted embodiment is burled. In the depicted embodiment, the knob-shaped gripping aid 6 is arranged essentially centrically below the palm space 4 on the periphery of the cuff 5. Contrary to the preferred embodiment in which a glove according to the invention may be worn ambilaterally, the depicted glove may only be worn on the left hand as the structured surfaces 9 are arranged on only one side at the ends 8 of the finger spaces 3, i.e. in a horizontally arranged glove with the thumb pointing to the left only at the upper side of the finger spaces 3.

FIG. 4 shows a further glove 1 according to the invention having a glove body 2 and a cuff 5. The glove body 2 comprises five finger spaces 3 which are connected to the palm space 4 each. At their ends 8 opposite the palm space 4, the finger spaces 3 have structured surfaces 9, respectively, in the shape of lamellae at a parallel spacing. The structured surfaces 9 are arranged partially circumferential at the ends 8 of the finger spaces 3 and extend over about half to one third of the length of the finger spaces 3 in the direction of the palm space 4.

An angularly arranged lobe-shaped gripping aid 6 is arranged at the cuff 5 which gripping aid also has lamellae essentially running in parallel as a structured surface 7.

FIG. 5 shows a former 10. Such a former is applicable in a process according to the invention for production of gloves according to the invention. Below the thumb and laterally of the wrist of the model hand of the former, the former has an elevation at its surface that is similar to a knob or to a truncated cone, respectively. Therefore, upon dipping of the former into an immersion bath the gripping aid is co-produced directly in the shaping phase at the respective position, i.e. laterally below the finger space which is adapted for intake of a thumb. Although it is not depicted in FIG. 5, the former is supposed to have patterning at its elevation as well as at least two fingers of the model hand in the region of the fingertips.

FIG. 6 shows a glove according to the invention having a gripping aid 6 which comprises a structured surface 7. Besides, the glove has structured surfaces 9 on each finger space at their ends opposite the palm space. On its side which is averted from the rolled edge, the gripping aid 6 is arranged on the periphery of the cuff such that the transition between the cuff 5 and the gripping aid 6 has a U-shaped profile. Accordingly, a former 10 also has this U-shaped profile, which former was used for producing the glove. Due to the U-shaped profile of the transition between the cuff 5 and the gripping aid 6, no air bubbles are formed during the dipping of the former 10 into an immersion bath, as they could be formed for example with an angular transition between the cuff 5 and the gripping aid 6. On its side facing the rolled edge, the gripping aid 6 also has a slight depression. The respective depression of the former 10 which was used for production of the glove effects that liquid increasingly accumulates in the depression during the dipping of the former 10 into an immersion bath or during the subsequent drying, respectively, in the production process according to the invention. Therefore, the glove preferably has an increased material thickness and resulting therefrom an increased tear strength in this region.

Furthermore, it is generally preferred that the gripping aid 6 has a protrusion (not depicted) which e.g. is arranged at an angle to its longitudinal direction, at which protrusion after the "dipping" liquid flowing down in a vertical position of the glove with the fingertips and finger spaces pointing downwards, respectively, accumulates instead of dripping off the gripping aid 6 (e.g. onto the finger space 3 which is adapted to a thumb).

LIST OF REFERENCE NUMERALS 1 glove
2 glove body
3 finger space
4 palm space
5 cuff
6 gripping aid
7 structured surface at the gripping aid
8 end of the finger space opposite the palm space
9 structured surface at the glove body
10 former

The invention claimed is:

1. A pair of gloves, comprising a first glove and an identical second glove, wherein each glove is an examination glove or surgical glove (1) having a glove body (2) which comprises five finger spaces (3) adapted for fingers of one hand of a wearer and a palm space (4) connected to each of the finger spaces (3), and having a cuff (5) adjoining to the palm space (4), wherein exactly one gripping aid (6) for removing the glove from a hand of the wearer is arranged on a periphery of said cuff (5), on the wherein the glove body (2), the cuff (5) and the gripping aid (6) are made in one piece, the gripping aid (6) at least partially has a nubby surface (7) and the glove body (2) has a nubby surface (9) at least at two of the finger spaces (3) at their respective ends (8) opposite the palm space (4), wherein the gripping aid (6) is arranged in a cuff region laterally of the wrist when the glove (1) is worn, wherein when the gripping aid (6) of the first glove is seized by a hand wearing the second glove (1), the nubby surfaces (9) at the ends (8) of the finger spaces (3) of the second glove interlock with the nubby surface (7) of the gripping aid (6) of the first glove, wherein the gripping aid (6) of each glove (1) is a lobe having a cavity which projects from the surface of the cuff (5), which, when each glove (1) is worn on the hand, unlike the rest of each glove (1) does not fit tight to the hand but is projecting from the surface of each glove (1), wherein the cavity is formed between an inner side of the lobe and adaptively the one hand of the wearer, wherein the gripping aid (6) measured from its attachment to the cuff (5) to its opposing end has a length in the range of 0.8 cm-2.2 cm, and wherein the nubby surfaces (9) at the ends (8) of the finger spaces (3) extend over 70 to 100% of a periphery of the finger spaces (3).

2. The pair of gloves according to claim 1, wherein the glove body (2) of each glove (1) has a nubby surface (9) at all five finger spaces (3) at their respective ends (8) opposite the palm space (4).

3. The pair of gloves according to claim 1, wherein the nubby surface (7, 9) comprises knobs, or grooves.

4. The pair of gloves according to claim 1, wherein each glove has a wall thickness and wherein at its end opposite the glove body (2) the cuff (5) has a rolled edge as an end, wherein the wall thickness of the glove in a region adjacent to the nubby surface (7) of the gripping aid (6) is increased in comparison to an adjacent region without a nubby surface and with the same distance to the rolled edge.

5. The pair of gloves according to claim 1, wherein the nubby surface (9) at the finger spaces (3) of each glove or the nubby surface (7) at the gripping aid (6) of each glove has a color which is different from the rest of the glove.

6. Process for producing the pair of gloves according to claim 1 using a former (10), wherein the gripping aid (6) of each glove with its at least partially nubby surface (7) as well as the nubby surfaces (9) at the finger spaces (3) of the glove body (2) of each glove are co-produced in the shaping process of each glove (1).

7. The process according to claim 6, characterized by the steps
- providing a former (10) having the geometry of a hand with an essentially cylindrical section adjoining thereto, at the periphery of which at least one elevation is arranged, wherein at the surface of the elevation patterning is arranged at least partially, and wherein at least two fingers of the model hand patterning is arranged, too, at their respective ends opposite the palm;
- dipping the former (10) into an immersion bath of chemical or natural ingredients;
- drying the glove (1);
- vulcanizing the glove (1);
- separating the glove (1) from the former (10).

\* \* \* \* \*

UNITED STATES PATENT AND TRADEMARK OFFICE
CERTIFICATE OF CORRECTION

PATENT NO. : 11,672,289 B2
APPLICATION NO. : 16/400630
DATED : June 13, 2023
INVENTOR(S) : Maxim Gleser and Paul Diers It is certified that error appears in the above-identified patent and that said Letters Patent is hereby corrected as shown below:

In the Claims

Column 14, Line 35, the text beginning with "a periphery of said cuff (5), on the wherein the glove body" in Claim 1 should read --a periphery of said cuff (5), wherein the glove body--.

Signed and Sealed this
Twenty-eighth Day of November, 2023

Katherine Kelly Vidal
*Director of the United States Patent and Trademark Office*